(12) United States Patent
Dandekar et al.

(10) Patent No.: US 7,671,248 B2
(45) Date of Patent: Mar. 2, 2010

(54) PROCESS FOR PRODUCING SEC-BUTYL BENZENE

(75) Inventors: Ajit B. Dandekar, Bridgewater, NJ (US); John P. McWilliams, Swedesboro, NJ (US); Thomas Francis Degnan, Jr., Moorestown, NJ (US); Michael Hryniszak, Bordentown, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 622 days.

(21) Appl. No.: 11/660,223

(22) PCT Filed: Aug. 5, 2005

(86) PCT No.: PCT/EP2005/008551

§ 371 (c)(1),
(2), (4) Date: Feb. 12, 2007

(87) PCT Pub. No.: WO2006/015824

PCT Pub. Date: Feb. 16, 2006

(65) Prior Publication Data

US 2008/0154082 A1 Jun. 26, 2008

Related U.S. Application Data

(60) Provisional application No. 60/601,468, filed on Aug. 13, 2004.

(51) Int. Cl.
C07C 2/58 (2006.01)

(52) U.S. Cl. .................................................. 585/467

(58) Field of Classification Search .................. 585/467
See application file for complete search history.

(56) References Cited

U.S. PATENT DOCUMENTS

| 4,992,606 A | 2/1991 | Kushnerick et al. |
| 5,059,736 A | 10/1991 | Tamura et al. |
| 5,334,795 A | 8/1994 | Chu et al. |
| 5,371,310 A | 12/1994 | Bennett et al. |
| 5,557,024 A | 9/1996 | Cheng et al. |
| 6,313,362 B1 | 11/2001 | Green et al. |

FOREIGN PATENT DOCUMENTS

| EP | 0 548 986 | 3/1996 |
| SU | 417405 | 8/1974 |
| SU | 372903 | 10/1974 |
| SU | 265349 | 10/1976 |
| SU | 1245564 | 7/1986 |
| WO | WO2004/052810 | 6/2004 |

OTHER PUBLICATIONS

"Catalytic properties of palladium-zeolite systems in the synthesis of sec-butylbenzene from benzene and ethylene," Isakov et al. Inst. Org. Khim, im. N. D. Zelinskogo, Moscow, Russia, Neftekhimiya (1994), 34(2), 151-70,(Abstract Only; XP002317126).

"Alkylation of benzene by ethylene on catalysts produced from synthetic zeolites ultrasil," Minachev et al., Inst. Org. Khim, im. Zelinskogo, Moscow, USSR, Neftekhimiya (1988), 28(2), 151-8 (Abstract Only: XP-002317128).

"Bifunctional catalysts for the alkylation of aromatic compounds by ethylene," Minachev et al., USSR, Lektsii-Vses, Shk. Katal, (1981), vol. 2, 76-111 (Abstract Only: XP-002317129).

"Study of the nature of bifunctional catalysts for the synthesis of sec-butylbenzene from ethylene and benzene, " Minachev et al. Inst. Org. Khim, im. Zelinskogo, Moscow, USSR, Geterog. Katal. (1979), $4_{th}$, Pt. 2, 485-92 (Abstract Only).

"Study of polyfunctional zeolite catalysts. Communication 2. Formation of a catalyst for synthesis off sec-butylbenzene prepared from nickel acetylacetonate and CaY zeolite," Isakov et al., Inst. Org. Khim. im. Zelinskogo, Moscow, USSR, Izv. Akad Nauk SSSR, Ser. Khim. (1976), (3), 498-504 (Abstract Only).

"Preparation of secondary butylbenzene from ethylene and benzene," Minachev et al., IOKh im. Zelinskogo, USSR, Neftepererabotka i Neftekhimiya (Moscow, Russian Federation) (1971), (9), 24-7 (Abstract Only: XP-002317127).

*Primary Examiner*—Thuan Dinh Dang

(57) ABSTRACT

A process for producing sec-butylbenzene comprises contacting a feed comprising benzene and ethylene under alkylation conditions with catalyst comprising (i) a molecular sieve having an X-ray diffraction pattern including d-spacing maxima at 12.4±0.25, 6.9±0.15, 3.57±0.07 and 3.42±0.07 Angstrom and (ii) at least one metal selected from Group 10 of the Periodic Table of Elements to produce an alkylation effluent comprising sec-butylbenzene.

31 Claims, No Drawings

PROCESS FOR PRODUCING SEC-BUTYL BENZENE

CROSS REFERENCE TO RELATED APPLICATIONS

This application is a 371 National Stage Application of International Application No. PCT/EP2005/008551, filed Aug. 5, 2005, which claims the benefit of Provisional Application No. 60/601,468, filed Aug. 13, 2004, the disclosures of which are herein incorporated by reference.

FIELD OF THE INVENTION

The present invention relates to a process for producing sec-butylbenzene.

BACKGROUND OF THE INVENTION

Sec-butylbenzene is useful as a starting material for the production of phenol and methyl ethyl ketone through the steps of air oxidation to the corresponding hydroperoxide followed by cleavage of the hydroperoxide. Phenol can be used as a solvent and in the production of phenol resins, bisphenol A, ε-caprolactam, adipic acid, alkyl phenols, and plasticizers, whereas methyl ethyl ketone can be used as a solvent for lacquers and resins and for dewaxing of lubricating oils.

The conventional route for the production of sec-butylbenzene involves alkylation of benzene with n-butene over a homogeneous catalyst, such as $AlCl_3$ or solid phosphoric acid. The product of the alkylation reaction is a mixture containing mainly sec-butylbenzene (SBB), isobutylbenzene (IBB), tert-butylbenzene, dibutylbenzenes (DSBB), and tributylbenzenes (TSBB). Of these compounds, dibutylbenzenes and tributylbenzenes are separated from the reaction mixture and can then transalkylated into sec-butylbenzene.

However, the boiling points of isobutylbenzene, sec-butylbenzene and tert-butylbenzene are 172.8° C., 173.5° C. and 169° C., respectively, and hence it is difficult to separate these compounds from each other by distillation. Moreover, isobutylbenzene and tert-butylbenzene are known to be inhibitors to the oxidation of sec-butylbenzene to the corresponding hydroperoxide. For example, the rate of oxidation of sec-butylbenzene, when the sec-butylbenzene contains 1% by weight of isobutylbenzene, decreases to about 91% of that when the sec-butylbenzene is free of isobutylbenzene. Similarly, when the isobutylbenzene content is 1.65% by weight, the rate of oxidation decreases to about 86%; when the isobutylbenzene content is 2% by weight, the rate of oxidation decreases to about 84%; and when the isobutylbenzene content is 3.5% by weight, the rate of oxidation decreases to as much as about 82%.

Therefore, in order to ensure the efficiency of the air oxidation step, it is important to minimize the amount of isobutylbenzene and tert-butylbenzene formed as by-products during the alkylation step to produce the sec-butylbenzene.

For example, U.S. Pat. No. 5,059,736 describes a process for producing sec-butylbenzene from benzene and n-butene, comprising reacting benzene and n-butene in the presence of a homogeneous liquid aluminum chloride complex catalyst, said catalyst comprising aluminum chloride, hydrogen chloride, and an aromatic hydrocarbon, wherein the amount of aluminum chloride used as a component of the complex catalyst is from 0.51 to 5% by weight of the benzene used, the reaction temperature is from 20° C. to 70° C., and the amount of isobutylbenzene formed as a by-product is such that the weight ratio of isobutylbenzene to sec-butylbenzene formed is not more than 0.01:1. However, as discussed above, even isobutylbenzene impurities of 1 wt % significantly inhibit the oxidation of sec-butylbenzene to the corresponding hydroperoxide.

U.S. Pat. No. 4,992,606 discloses a process for preparing short chain alkyl aromatic compounds which comprises contacting at least one alkylatable aromatic compound with at least one alkylating agent possessing an aliphatic group having from 1 to 5 carbon atoms under alkylation reaction conditions and in the presence of an alkylation catalyst to provide an alkylated aromatic product possessing at least one alkyl group derived from said alkylating agent, said catalyst comprising a synthetic porous crystalline material known as MCM-22. Similar disclosures are contained in U.S. Pat. Nos. 5,371,310 and 5,557,024 but where the synthetic porous crystalline material is MCM-49 and MCM-56 respectively.

U.S. Pat. No. 5,334,795 discloses a process for the production of ethylbenzene comprising alkylating benzene with ethylene under liquid phase conditions in the presence of a solid, porous acidic alkylation catalyst comprising MCM-22.

International Patent Application No. PCT/US2003/038709, published as WO 2004/052810. discloses a method for alkylating benzene with ethylene in the presence of metal-impregnated MCM-22. The catalysts are selective for mono-ethylbenzene over di- or tri-ethylbenzene.

In an article entitled "Catalytic Properties of Palladium-Zeolite Systems in the Synthesis of Sec-Butylbenzene from Benzene and Ethylene", Inst Org. Khim. im N. D. Zelinskogo, Moscow, Russia, Neftekhimiya (1994), 34(2), 151-70, Isakov et al. report that various palladium-containing zeolites (HY, cation-exchanged or dealuminated Mn+NaY, H-pentasil) are effective in the alkylation of benzene with ethylene to produce predominantly sec-butylbenzene or sec-butylbenzene. However, the article also reports that the product contains $C_4$-$C_6$ alkenes.

According to the present invention, it has been found that sec-butylbenzene that is substantially free of isobutylbenzene and tert-butylbenzene can be produced in high yield by the alkylation of benzene with ethylene in the presence of catalyst comprising an MCM-22 family zeolite and at least one metal cation selected from Group 10 of the Periodic Table of Elements. Moreover, the alkylation is accompanied by little or no production of ethylene oligomers, such as $C_4$-$C_6$ alkenes.

SUMMARY OF THE INVENTION

The invention resides in a process for producing sec-butylbenzene comprising contacting a feed comprising benzene and ethylene under alkylation conditions with catalyst comprising (i) a molecular sieve having an X-ray diffraction pattern including d-spacing maxima at 12.4±0.25, 6.9±0.15, 3.57±0.07 and 3.42±0.07 Angstrom and (ii) at least one metal selected from Group 10 of the Periodic Table of Elements to produce an alkylation effluent comprising sec-butylbenzene.

Conveniently, said sec-butylbenzene in said alkylation effluent contains less than 0.5 wt %, for example less than 0.1 wt %, such as less than 0.05 wt %, of isobutylbenzene and tert-butylbenzene.

Conveniently, the molecular sieve is selected from MCM-22, PSH-3, SSZ-25, ERB-1, ITQ-1, ITQ-2, MCM-36, MCM-49, MCM-56, UZM-8, and mixtures thereof. "Mixtures" as used here and throughout this specification and the appendant claims means any two or more items from the relevant list.

Conveniently, the metal is palladium. In one embodiment, the metal is present in an amount of at least 0.5% by weight of the catalyst.

Conveniently, the benzene and ethylene are contacted with the catalyst at a benzene:ethylene molar ratio between about 10:1 and about 1:10, such as between about 4:1 and about 1:4, for example between about 4:1 and about 1:1.

In one embodiment, said contacting is conducted under at least partial liquid phase conditions. Conveniently, said alkylation conditions include a temperature of from about 0° C. to about 350° C., such as from about 30° C. to about 300° C., a pressure of from about 10 to about 10,000 kPa, and an ethylene weight hourly space velocity (WHSV) of from about 0.1 to about 10 $hr^{-1}$.

In one embodiment, said alkylation effluent comprises polybutylbenzenes and the process further comprises contacting said polybutylbenzenes with benzene in the presence of a transalkylation catalyst to produce sec-butylbenzene. Conveniently, the transalkylation catalyst comprises a molecular sieve selected from zeolite beta, mordenite, USY, MCM-68, MCM-22, PSH-3, SSZ-25, ERB-1, ITQ-1, ITQ-2, MCM-36, MCM-49, MCM-56, UZM-8, and mixtures thereof.

In one embodiment, at least part of the sec-butylbenzene in said alkylation effluent is oxidized to produce a hydroperoxide and the hydroperoxide is cleaved to produce phenol and methyl ethyl ketone.

DETAILED DESCRIPTION OF THE EMBODIMENTS

The present invention is directed to a process for producing sec-butylbenzene by the reaction of ethylene with benzene. The reaction is conducted in the presence of a catalyst comprising (i) a molecular sieve having an X-ray diffraction pattern including d-spacing maxima at 12.4±0.25, 6.9±0.15, 3.57±0.07 and 3.42±0.07 Angstrom and (ii) at least one metal cation selected from Group 10 of the Periodic Table of Elements, advantageously palladium. Using such a catalyst, it is found that sec-butylbenzene can be produced in high yield and with very low concentration (less than 0.5 wt %) of isobutylbenzene and tert-butylbenzene. The resultant sec-butylbenzene is therefore a desirable feedstock for use in the modified Hock Process to produce to phenol and methyl ethyl ketone.

The benzene employed in the process of the invention can be any commercially available benzene feed, but preferably the benzene has a purity level of at least 99 wt %. Similarly any commercially available source of ethylene can be used, such as the mixed olefinic $C_2$ streams that can be obtained by the steam cracking of ethane, propane, butane, LPG and light naphthas, the catalytic cracking of naphthas and other refinery feedstocks and by the conversion of oxygenates, such as methanol, to lower olefins.

Conveniently, the total feed to the process of the present invention contains less than 1000 ppm, such as less than 500 ppm, for example less than 100 ppm, water. In addition, the total feed typically contains less than 100 ppm, such as less than 30 ppm, for example less than 3 ppm, sulfur and less than 10 ppm, such as less than 1 ppm, for example less than 0.1 ppm, nitrogen. It may, therefore, be advantageous to subject the benzene and/or ethylene to a prior treatment step or steps to reduce the amount of any water, sulfur or nitrogen therein. Pretreatment may also be useful to remove unreacted oxygenates which may, for example, be present in ethylene streams obtained by oxygenate conversion processes. Removal of sulfur, nitrogen and oxygenate impurities is conveniently effected by one or a combination of caustic treatment, water washing, distillation, adsorption using molecular sieves and/or membrane separation. Water is also typically removed by adsorption.

The catalyst used in the present process comprises a crystalline molecular sieve having an X-ray diffraction pattern including d-spacing maxima at 12.4±0.25, 6.9±0.15, 3.57±0.07 and 3.42±0.07 Angstrom. The X-ray diffraction data used to characterize the molecular sieve are obtained by standard techniques using the K-alpha doublet of copper as the incident radiation and a diffractometer equipped with a scintillation counter and associated computer as the collection system.

Materials having said X-ray diffraction pattern are sometimes referred to a molecular sieves of the MCM-22 family and include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-I (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and mixtures thereof.

The alkylation catalyst can include the molecular sieve in unbound or self-bound form or, alternatively, the molecular sieve can be combined in a conventional manner with an oxide binder, such as alumina, such that the final alkylation catalyst contains between 2 and 80 wt % sieve.

In addition to the molecular sieve and any binder, the catalyst used in the present process includes at least one metal selected from Group 10 (such as Pt and Pd) of the Periodic Table of Elements. The preferred metal is palladium. The metal can be present in the catalyst in elemental form or as a compound, such as an oxide, of the metal. Typically, the catalyst contains at least 0.5% by weight, for example from about 0.5% to about 5% by weight, such as about 1% to about 4% by weight, of the metal. The metal can be introduced into the catalyst by any known technique such as, for example, impregnation and ion exchange.

The alkylation process is conducted such that the organic reactants, i.e., the benzene and ethylene, are brought into contact with an alkylation catalyst in a suitable reaction zone such as, for example, in a flow reactor containing a fixed bed of the catalyst composition or in a catalytic distillation reactor, under effective alkylation conditions. Such conditions include a temperature of from about 0° C. to about 350° C., for example between about 30° C. and about 300° C., a pressure of about 10 to about 10,000 kPa, for example from about 100 to about 5,000 kPa, and a weight hourly space velocity (WHSV) based on ethylene of between about 0.1 and about 50 $hr^{-1}$, for example between about 1 and about 10 $hr^{-1}$. Typically, the molar ratio of benzene to ethylene is between about 10:1 and about 1:10, such as between about 4:1 and about 1:4, for example between about 4:1 and about 1:1.

The reactants can be in either the vapor phase or partially or completely in the liquid phase and can be neat, i.e., free from intentional admixture or dilution with other material, or they can be brought into contact with the zeolite catalyst composition with the aid of carrier gases or diluents such as, for example, hydrogen or nitrogen.

Using the catalyst described above, it is found that the alkylation step of the process of the invention is highly selective to sec-butylbenzene. In particular, it is found that the sec-butylbenzene produced normally contains less than 0.5 wt %, for example, less than 0.1 wt %, such as less than 0.05 wt %, of isobutylbenzene or tert-butylbenzene.

Although the alkylation step is highly selective towards sec-butylbenzene, the effluent from the alkylation reaction will normally contain some polyalkylated products, as well as unreacted aromatic feed and the desired monoalkylated species. The unreacted aromatic feed is normally recovered by distillation and recycled to the alkylation reactor. The bottoms from the benzene distillation are further distilled to separate monoalkylated product from any polyalkylated products and other heavies. Depending on the amount of polyalkylated products present in the alkylation reaction effluent, it may be desirable to transalkylate the polyalkylated products with additional benzene to maximize the production of the desired monoalkylated species.

Transalkylation with additional benzene is typically effected in a transalkylation reactor, separate from the alkylation reactor, over a suitable transalkylation catalyst, such as an MCM-22 family catalyst, zeolite beta, MCM-68 (see U.S. Pat. No. 6,014,018), zeolite Y and mordenite. The transalkylation reaction is typically conducted under at least partial liquid phase conditions, which suitably include a temperature of 100 to 300° C., a pressure of 1000 to 7000 kPa, a weight hourly space velocity of 1 to 50 $hr^{-1}$ on total feed, and a benzene/polyalkylated benzene weight ratio of 1 to 10.

Since the sec-butylbenzene produced by the alkylation process of the invention is substantially free of isobutylbenzene or tert-butylbenzene, it provides an advantageous feed for use in the modified Hock Process to produce phenol and methyl ethyl ketone. In this process the sec-butylbenzene is initially oxidized to the corresponding hydroperoxide and then the hydroperoxide is cleaved to produce phenol and methyl ethyl ketone.

Oxidation of sec-butylbenzene to the corresponding hydroperoxide is conveniently accomplished by introducing an oxygen-containing gas, such as air, into a liquid phase containing the sec-butylbenzene. The reaction can be performed in the absence of a catalyst but is slow (of the order of <1%/hour at atmospheric conditions). Improvement in the reaction rate can be achieved by performing the oxidation in the presence of a catalyst, such as a water-soluble chelate compound in which multidentate ligands are coordinated to at least one metal from cobalt, nickel, manganese, copper, and iron. (See U.S. Pat. No. 4,013,725). More preferably, a heterogeneous catalyst is used. Suitable heterogeneous catalysts are described in U.S. Pat. No. 5,183,945, wherein the catalyst is an oxo (hydroxo) bridged tetranuclear manganese complex and in U.S. Pat. No. 5,922,920, wherein the catalyst comprises an oxo (hydroxo) bridged tetranuclear metal complex having a mixed metal core, one metal of the core being a divalent metal selected from Zn, Cu, Fe, Co, Ni, Mn and mixtures thereof and another metal being a trivalent metal selected from In, Fe, Mn, Ga, Al and mixtures thereof. The entire disclosures of said U.S. patents are incorporated herein by reference.

Other suitable catalysts for sec-butylbenzene oxidation are the N-hydroxy substituted cyclic imides described in Published U.S. Patent Application No. 2003/0083527 and incorporated herein by reference, such as N-hydroxyphthalimide, 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, N,N'-dihydroxy(pyromellitic diimide), N,N'-dihydroxy(benzophenone-3,3',4,4'-tetracarboxylic diimide), N-hydroxymaleimide, pyridine-2,3-dicarboximide, N-hydroxysuccinimide, N-hydroxy(tartaric imide), N-hydroxy-5-norbornene-2,3-dicarboximide, exo-N-hydroxy-7-oxabicyclo[2.2.1]hept-5-ene-2,3-dicarboximide, N-hydroxy-cis-cyclohexane-1,2-dicarboximide, N-hydroxy-cis-4-cyclohexene-1,2 dicarboximide, N-hydroxynaphthalimide sodium salt or N-hydroxy-o-benzenedisulphonimide. These materials can be used either alone or in the presence of a free radical initiator and can be used as liquid-phase, homogeneous catalysts or can be supported on a solid carrier to provide a heterogeneous catalyst.

Suitable conditions for sec-butylbenzene oxidation include a temperature between about 70° C. and about 200° C., such as about 90° C. to about 130° C. and a pressure of about 0.5 to about 10 atmospheres (50 to 1000 kPa). A basic buffering agent may be added to react with acidic by-products that may form during the oxidation. In addition, an aqueous phase may be introduced, which can help dissolve basic compounds, such as sodium carbonate. The per-pass conversion in the oxidation step is preferably kept below 50%, to minimize the formation of byproducts. The oxidation reaction is conveniently conducted in a catalytic distillation unit and the sec-butylbenzene hydroperoxide produced may be concentrated by distilling off the unreacted sec-butylbenzene prior to the cleavage step.

Cleavage of sec-butylbenzene hydroperoxide to produce the desired phenol and methyl ethyl ketone can be effected by contacting the sec-butylbenzene hydroperoxide with a catalyst in the liquid phase at a temperature of about 20° C. to about 150° C., such as about 40° C. to about 120° C., a pressure of about 50 to about 2500 kPa, such as about 100 to about 1000 kPa and a liquid hourly space velocity (LHSV) based on the hydroperoxide of about 0.1 to about 100 $hr^{-1}$, preferably about 1 to about 50 $hr^{-1}$. The sec-butylbenzene hydroperoxide is preferably diluted in an organic solvent inert to the cleavage reaction, such as methyl ethyl ketone, phenol or sec-butylbenzene, to assist in heat removal. The cleavage reaction is conveniently conducted in a catalytic distillation unit.

The catalyst employed in the cleavage step can be a homogeneous catalyst or a heterogeneous catalyst.

Suitable homogeneous cleavage catalysts include sulfuric acid, perchloric acid, phosphoric acid, hydrochloric acid and p-toluenesulfonic acid. Ferric chloride, boron trifluoride, sulfur dioxide and sulfur trioxide are also effective homogeneous cleavage catalysts. The preferred homogeneous cleavage catalyst is sulfuric acid A suitable heterogeneous catalyst for use in the cleavage of sec-butylbenzene hydroperoxide includes a smectite clay, such as an acidic montmorillonite silica-alumina clay, as described in U.S. Pat. No. 4,870,217, the entire disclosure of which is incorporated herein by reference.

The following examples are given for illustrative purposes and do not limit the scope of the invention.

Example 1

An MCM-22 catalyst was prepared by extruding 65 wt % MCM-22 crystal with 35 wt % alumina into ⅟₁₆" (1.6 mm) extrudate. One gram of the catalyst was charged to an isothermal well-mixed Parr autoclave reactor along with a mixture comprising of benzene (195 grams) and ethylene (20 grams). The reaction was carried out at 428° F. (220° C.) and 550 psig (3893 kPa) for 4 hours. A small sample of the product was withdrawn at regular intervals and analyzed by gas chromatography. The catalyst performance was assessed by a kinetic rate constant evaluated on the basis of ethylene conversion, and ethylbenzene and sec-butylbenzene selectivities at 100% ethylene conversion, and is described in Example 8.

Example 2

5.2 grams of $(NH_4)_6Mo_7O_{24} \cdot 4H_2O$ were dissolved in 50 grams of distilled water to yield a solution of pH=5.54. The resulting solution was used to impregnate fifty grams of a fresh sample of MCM-22 using an incipient wetness method. The impregnated catalyst was dried at 250° F. (121° C.) for 12 hours in air followed by calcination at 680° F. (360° C.) in flowing air for 4 hours. One gram of the final catalyst was evaluated for benzene alkylation with ethylene according to the procedure described in Example 1. Catalyst performance is compared with unmodified MCM-22 in Example 8.

Example 3

0.58 grams of $NH_4ReO_7$ were dissolved in 50 grams of distilled water to yield a solution of pH=6.09. The resulting solution was used to impregnate fifty grams of a fresh sample of MCM-22 using an incipient wetness method. The impregnated catalyst was dried at 250° F. (121° C.) for 12 hours in air followed by calcination at 680° F. (360° C.) in flowing air for 4 hours. One gram of the final catalyst was evaluated for benzene alkylation with ethylene according to the procedure described in Example 1. Catalyst performance is compared with unmodified MCM-22 in Example 8.

Example 4

1.54 grams of $(NH_3)_6RuCl_3$ were dissolved in 50 grams of distilled water to yield a solution of pH=2.1. The resulting solution was used to impregnate fifty grams of a fresh sample of MCM-22 using an incipient wetness method. The impregnated catalyst was dried at 250° F. (121° C.) for 12 hours in air followed by calcination at 680° F. (360° C.) in flowing air for 4 hours. One gram of the final catalyst was evaluated for benzene alkylation with ethylene according to the procedure described in Example 1. Catalyst performance is compared with unmodified MCM-22 in Example 8.

Example 5

0.64 grams of $H_2IrCl_6$ were dissolved in 50 grams of distilled water to yield a solution of pH=6.9. The resulting solution was used to impregnate fifty grams of a fresh sample of MCM-22 using an incipient wetness method. The impregnated catalyst was dried at 250° F. (121° C.) for 12 hours in air followed by calcination at 680° F. (360° C.) in flowing air for 4 hours. One gram of the final catalyst was evaluated for benzene alkylation with ethylene according to the procedure described in Example 1. Catalyst performance is compared with unmodified MCM-22 in Example 8.

Example 6

12.6 grams of $(NH_3)_6Pt(NO_3)_2$ were dissolved in 50 grams of distilled water to yield a solution of pH=5.36. The resulting solution was used to impregnate fifty grams of a fresh sample of MCM-22 using an incipient wetness method. The impregnated catalyst was dried at 250° F. (121° C.) for 12 hours in air followed by calcination at 680° F. (360° C.) in flowing air for 4 hours. One gram of the final catalyst was evaluated for benzene alkylation with ethylene according to the procedure described in Example 1. Catalyst performance is compared with unmodified MCM-22 in Example 8.

Example 7

10.2 grams of $(NH_3)_4Pd(NO_3)_2$ were dissolved in 50 grams of distilled water to yield a solution of pH=8.1. The resulting solution was used to impregnate fifty grams of a fresh sample of MCM-22 using an incipient wetness method. The impregnated catalyst was dried at 250° F. (121° C.) for 12 hours in air followed by calcination at 680° F. (360° C.) in flowing air for 4 hours. One gram of the final catalyst was evaluated for benzene alkylation with ethylene according to the procedure described in Example 1. Catalyst performance is compared with unmodified MCM-22 in Example 8.

Example 8

The performance of MCM-22 modified with a transition metal from Groups 6 through 10 is compared with unmodified MCM-22 in Table 1 below.

TABLE 1

| Example | Metal | Kinetic Rate Constant | Ethylbenzene (wt %) | Sec-Butylbenzene (wt %) |
|---|---|---|---|---|
| 1 | None | 41 | 91.9 | 0.3 |
| 2 | Mo | 5 | 91.1 | 4.0 |
| 3 | Re | 37 | 89.7 | 5.0 |
| 4 | Ru | 60 | 83.8 | 11.8 |
| 5 | Ir | 82 | 77.7 | 18.2 |
| 6 | Pt | 190 | 65.1 | 31.5 |
| 7 | Pd | 360 | 0.5 | 99.5 |

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A process for producing sec-butylbenzene containing less than 0.5 wt % isobutylbenzene and tert-butylbenzene, comprising contacting a feed comprising benzene and ethylene under alkylation conditions to react benzene with ethylene with catalyst comprising (i) a molecular sieve having an X-ray diffraction pattern including d-spacing maxima at 12.4±0.25, 6.9±0.15, 3.57±0.07 and 3.42±0.07 Angstrom and (ii) palladium to produce an alkylation effluent comprising the sec-butylbenzene.

2. The process of claim 1, wherein the sec-butylbenzene in the alkylation effluent contains less than 0.1 wt %, 0.05 wt %, of isobutylbenzene and tert-butylbenzene.

3. The process of claim 1, wherein the molecular sieve is selected from the group consisting of MCM-22, PSH-3, SSZ-25, ERB-1, ITQ-1, ITQ-2, MCM-36, MCM-49, MCM-56, UZM-8, and mixtures thereof.

4. The process of claim 1, wherein the palladium is present in an amount of at least 0.5% by weight of the catalyst.

5. The process of claim 4, wherein the palladium is present in an amount of from about 0.5% to about 5% by weight of the catalyst.

6. The process of claim 1, wherein the ethylene is contained in a mixed $C_2$ hydrocarbon stream.

7. The process of claim 6, wherein the mixed $C_2$ hydrocarbon stream is derived from steam cracking, catalytic cracking or an oxygenate to olefin conversion process.

8. The process of claim 1, wherein the feed comprises less than 1000 ppm of water.

9. The process of claim 1, wherein the feed comprises less than 100 ppm of sulfur.

10. The process of claim 1, wherein the feed comprises less than 10 ppm of nitrogen.

11. The process of claim 1, wherein the benzene and ethylene are contacted with the catalyst at a benzene:ethylene molar ratio between about 10:1 and about 1:10.

12. The process of claim 1, wherein said contacting is conducted under at least partial liquid phase conditions.

13. The process of claim 1, wherein said contacting is conducted by catalytic distillation.

14. The process of claim 1, wherein said alkylation conditions include a temperature of about 0° C. to about 350° C., a pressure of about 10 to about 10,000 kPa, and an ethylene weight hourly space velocity (WHSV) of about 0.1 to about 50 $hr^{-1}$.

15. The process of claim 14, wherein said alkylation conditions include a temperature of from about 30° C. to about 300° C., a pressure of from about 100 to about 5,000 kPa, and an ethylene weight hourly space velocity (WHSV) of from about 1 to about 10 $hr^{-1}$.

16. The process of claim 1, wherein said alkylation effluent comprises polybutylbenzenes and the process further comprises contacting said polybutylbenzenes with benzene in the presence of a transalkylation catalyst to produce sec-butylbenzene.

17. The process of claim 16, wherein the transalkylation catalyst comprises a molecular sieve selected from the group consisting of zeolite beta, mordenite, USY, MCM-68, MCM-22, PSH-3, SSZ-25, ERB-1, ITQ-1, ITQ-2, MCM-36, MCM-49, MCM-56, UZM-8, and mixtures thereof.

18. The process of claim 1 and further comprising oxidizing at least part of the sec-butylbenzene in said alkylation effluent to produce a hydroperoxide.

19. The process of claim 18, wherein said oxidizing is conducted in the presence of a catalyst.

20. The process of claim 19, wherein said oxidation catalyst is selected from:
   (a) an oxo (hydroxo) bridged tetranuclear metal complex comprising manganese,
   (b) an oxo (hydroxo) bridged tetranuclear metal complex having a mixed metal core, one metal of the core being a divalent metal selected from Zn, Cu, Fe, Co, Ni, Mn and mixtures thereof and another metal being a trivalent metal selected from In, Fe, Mn, Ga, Al and mixtures thereof and
   (c) an N-hydroxy substituted cyclic imide either alone or in the presence of a free radical initiator.

21. The process of claim 18, wherein the oxidizing is conducted at a temperature of about 70° C. to about 200° C. and a pressure of about 0.5 to about 10 atmospheres (50 to 1000 kPa).

22. The process of claim 18, wherein said oxidizing is conducted by catalytic distillation.

23. The process of claim 18 and further comprising cleaving at least part of the hydroperoxide to produce phenol and methyl ethyl ketone.

24. The process of claim 23, wherein the cleaving is conducted in the presence of a catalyst.

25. The process of claim 23, wherein the cleaving is conducted in the presence of a homogeneous catalyst.

26. The process of claim 25, wherein said homogeneous catalyst comprises at least one of sulfuric acid, perchloric acid, phosphoric acid, hydrochloric acid, p-toluenesulfonic acid, ferric chloride, boron trifluoride, sulfur dioxide and sulfur trioxide.

27. The process of claim 25, wherein said homogeneous catalyst comprises sulfuric acid.

28. The process of claim 24, wherein the cleaving is conducted in the presence of a heterogeneous catalyst.

29. The process of claim 28, wherein said heterogeneous catalyst comprises a smectite clay.

30. The process of claim 23, wherein said cleaving is conducted by catalytic distillation.

31. The process of claim 23, wherein the cleaving is conducted at a temperature of about 40° C. to about 120° C., a pressure of about 100 to about 1000 kPa, and a liquid hourly space velocity (LHSV) based on the hydroperoxide of about 1 to about 50 $hr^{-1}$.

* * * * *